United States Patent [19]

Wheeler et al.

[11] Patent Number: 5,478,860
[45] Date of Patent: Dec. 26, 1995

[54] STABLE MICROEMULSIONS FOR HYDROPHOBIC COMPOUND DELIVERY

[75] Inventors: Jeffery J. Wheeler, Vancouver; Marcel B. Bally, Bowen Island, both of Canada

[73] Assignee: Inex Pharmaceuticals Corp., Vancouver, Canada

[21] Appl. No.: 71,724

[22] Filed: Jun. 4, 1993

[51] Int. Cl.⁶ ................................................ A61K 31/335
[52] U.S. Cl. ........................ 514/449; 424/455; 424/484; 549/510
[58] Field of Search ................. 514/449; 549/510; 424/455, 484

[56] References Cited

U.S. PATENT DOCUMENTS

| | | | |
|---|---|---|---|
| 4,534,899 | 8/1985 | Sears | 260/403 |
| 5,254,580 | 10/1993 | Chen et al. | 514/449 |
| 5,278,324 | 1/1994 | Kingston et al. | 549/510 |
| 5,283,253 | 2/1995 | Holton et al. | 514/444 |

FOREIGN PATENT DOCUMENTS

| | | |
|---|---|---|
| 5103356 | 10/1992 | European Pat. Off. . |
| 93/24476 | 12/1993 | WIPO . |

*Primary Examiner*—Richard L. Raymond
*Attorney, Agent, or Firm*—Townsend and Townsend and Crew

[57] ABSTRACT

Microemulsion compositions for the delivery of hydrophobic compounds are provided. Such compositions have a variety of uses. In one embodiment, the hydrophobic compounds are therapeutic agents including drugs. The present invention also discloses methods for in vitro and in vivo delivery of hydrophobic compounds to cells. Uses of the methods in vitro include the testing of hydrophobic compounds for cytotoxicity. Uses of the methods in vivo include diagnostic and therapeutic purposes.

18 Claims, 8 Drawing Sheets

STABLE MICROEMULSIONS FOR HYDROPHOBIC COMPOUND DELIVERY

TECHNICAL FIELD

The present invention relates generally to the delivery of hydrophobic compounds to cells. This invention is more particularly related to compositions containing hydrophobic compounds in microemulsion carriers, and the use of such compositions in methods for the delivery of hydrophobic compounds to cells.

BACKGROUND OF THE INVENTION

The isolation or synthesis of new compounds potentially useful in the treatment of a variety of diseases has increased substantially over the years. Despite the availability of new compounds, their use is hampered by the fact that many are not water-soluble and thus require a carrier for transportation in aqueous environments. A carrier needs to be both safe and effective. The use of current carders is limited by toxicity problems (such as the induction of hypersensitivity reactions) and/or stability problems.

One example of a compound which, due to its unique solubility characteristics, must be formulated in a carrier is taxol. A diterpenoid derived from the bark of the Pacific Yew (Taxus brevifolia, Nutt), taxol is an exciting new anti-cancer drug with proven activity in the treatment of ovarian cancer. Despite the great interest in development of the drug for treatment of cancer, several significant obstacles have arisen concerning its use.

Taxol is formulated in cremophor EL, a common lipid emulsion used for hydrophobic drugs. Cremophor EL is polyoxyethylated castor oil in anhydrous ethanol (50:50). It is well established, however, that the solubilizing agent cremophor EL can promote acute toxic reactions typically expressed as hypersensitivity (Lassus et al., *Proc. Am. Soc. Oncol.* 4:268, 1985). At present, this is managed clinically though the use of premedication regimes with anti-inflammatory agents such as corticosteroids, antihistamines, dexamethasone and diphenhydramine. Even with premedication, 41% of all patients will exhibit a hypersensitivity reaction (Taxol package insert from Bristol-Myers Squibb; also, Kris et al., *Cancer Treatment Reports* 70(5):605, 1986). In order to reduce acute reactions to the present taxol formulation, the drug has to be given by intravenous infusion, typically over 24 hours. This step adds significantly to the cost of patient care.

An additional problem relates to the fact that the present formulation of taxol is very effective at extracting plasticizers, such as di-(2-ethylhexyl) phthalate from PVC infusion bags and tubing (Taxol package insert; and Waugh et al., *American Journal of Hospital Pharmacists* 48:1520, 1991). These plasticizers are known to promote toxic reactions, such as Adult Respiratory Distress Syndrome (ARDS), in patients which have been exposed to high levels. The present taxol formulation must be stored in glass or polypropylene bottles or bags and should be administered through polyethylenelined tubing. Thus the current formulation of taxol requires a lengthy infusion time and extra care in storage and administration, which adds substantially to the cost of the treatment. Taxol is an example of the need for a better formulation for hydrophobic compounds such as drugs.

Due to the difficulties in the current approaches to the delivery of hydrophobic compounds to the site of desired activity, there is a need in the art for improved compositions and methods. The present invention fulfills this need, and further provides other related advantages.

SUMMARY OF THE INVENTION

Briefly stated, in one aspect, the present invention provides compositions useful for the delivery of hydrophobic compounds to cells. While previous formulations relied on the intrinsic ability of lipids to solubilize hydrophobic drugs, a decrease in the acute toxicity of hydrophobic drug formulations has now been effected in the present invention. A microemulsion composition of the present invention comprises a mixture of an oil, a hydrophobic compound, and a polyethylene glycol-linked lipid, wherein the mixture is surrounded by a monolayer of a polar lipid. In one embodiment, the mixture further includes a phospholipid. In a preferred embodiment, the hydrophobic compound is a therapeutic agent.

In another aspect, the present invention provides a method for delivering a compound to cells in vitro. The method comprises contacting cells with a microemulsion composition under conditions and for a time sufficient to allow delivery of a hydrophobic compound to the cells, wherein the microemulsion comprises a mixture of an oil, a hydrophobic compound, and a polyethylene glycol-linked lipid, and wherein the mixture is surrounded by a monolayer of a polar lipid.

In a related aspect, the present invention provides a method for delivering a hydrophobic compound to cells in vivo. The method comprises administering to a warm-blooded animal a microemulsion composition comprising a mixture of an oil, a hydrophobic compound, and a polyethylene glycol-linked lipid, wherein the mixture is surrounded by a monolayer of a polar lipid.

These and other aspects of the present invention will become evident upon reference to the following detailed description and attached drawings.

DETAILED DESCRIPTION OF THE INVENTION

Figure 2:
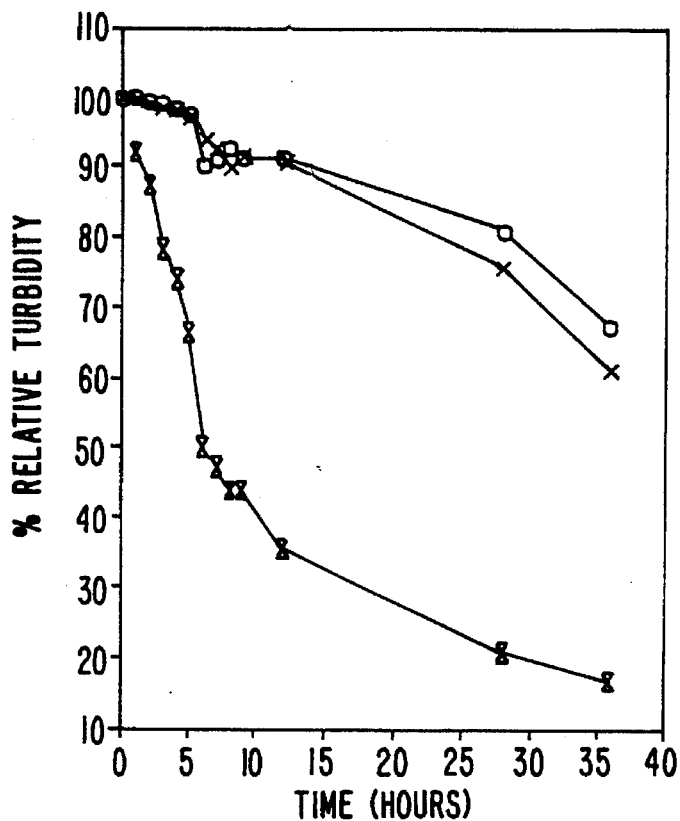
FIG. 2 graphically depicts the stability of oil emulsions coated with MePEGS-2000-DSPE. The emulsions were prepared and analyzed as in FIG. 1. ✕ no phospholipid; ☐ 7% MePEGS-2000-DSPE; and →←  10% MePEGS-2000-DSP.

As noted above, the present invention is directed toward compositions and methods for the delivery of hydrophobic compounds to sites located in aqueous environments. The compositions of the present invention are microemulsions, as opposed to systems such as liposomes or micelles. The disclosure of the present invention shows that microemulsion compositions containing a hydrophobic compound can be prepared in a manner such that they are both safe and effective. In particular, compositions of the present invention, which contain a hydrophobic drug, when administered in vivo do not elicit the adverse effects observed by administration of other preparations currently available which contain the drug at equivalent or lower concentrations. Further, compositions of the present invention have good stability which permits delivery to a desired site without significant premature release of free compound.

A microemulsion composition of the present invention comprises a mixture of an oil, a hydrophobic compound, and a polyethylene glycol-linked lipid, where the mixture is surrounded by a monolayer of a polar lipid. In such compositions, a hydrophobic compound resides in an oil environment which is surrounded by a monolayer of a polar lipid. The polar "head" of a lipid faces out (i.e., away from the internal oil environment) to provide compatibility with an external aqueous environment and the nonpolar "tail" of a lipid faces inward for compatibility with the internal oil environment. A polyethylene glycol-linked lipid is present to enhance the stability of the microemulsion compositions.

A variety of oils are suitable for use in the present compositions. In one embodiment, the oil is derived from a plant. For example, corn oil is an acceptable pharmaceutical vehicle. Corn oil is composed of fatty acids present as glycerides, which are typically proportioned as 43.3% oleic acid, 39.1% linoleic acid, 7.3% palmitic acid, 3.3% stearic acid, 0.4% arachidic acid, and 0.2% lignoceric acid. In small amounts, phosphatides, carbohydrates, and coloring matter are also present. Oils which may be used in place of corn oil may be sources from soya beans, safflower plants, sunflowers, olives, and other natural sources. Natural oils are commercially available, e.g., from U.S. Biochemicals Corp. (Cleveland, Ohio) or Ruger Chemical Co. (Hillside, N.J.) In addition, synthetic oils, e.g., comprising triacylglycerides with free fatty acid, may also be used. Synthetic oils are also commercially available, e.g., from Sigma Chemical Co. (St. Louis, Mo.).

A variety of polyethylene glycol ("PEG")-linked lipids are suitable for use in the present invention. For example, a PEG-linked lipid may contain acyl groups such as myristoyl (14:0), palmitoyl (16:0), stearoyl (18:0), oleoyl (18:1) or combinations thereof (e.g., 1-palmitoyl-2-oleoyl). Further, a PEG-linked lipid may contain lipids with amino, hydroxyl or sulfhydryl groups. PEG-linked lipids are commercially available (e.g., Avanti Polar Lipids, Inc., Alabaster, Ala.) or may be synthesized (e.g., using the methods described herein). It is desirable that a PEG-linked lipid impart to the compositions a hydrophilic shell and good stability. The stability of a composition of the present invention may be readily tested in vitro. If a microemulsion is not stable, the oil will coalesce and this is detectable, for example, as a change in the turbidity. The turbidity of a sample may be measured, for example, by spectrophotometry (e.g., at 640 nm). Another way to assess stability is by confirming that the hydrophobic compound remains associated with the composition. For example, column chromatography may be used to demonstrate coelution of a hydrophobic compound with a microemulsion composition. It will be evident to those of ordinary skill in the art that a variety of means (e.g., reporter groups such as radioactive molecules) exist by which to track a hydrophobic compound and a microemulsion carrier. In general, PEG-linked lipids will range in molecular weight from about 500 to 20,000. A preferred molecular weight range is from about 500 to 5,000. Preferred PEG-linked lipids include PEGs linked to a phosphatidylethanolamine. Examples of such PEG-linked lipids include MePEGS-5000-palmitoyl oleyl phosphatidylethanolamine and MePEGS-2000-distearoyl phosphatidylethanolamine.

A hydrophobic compound is a compound with limited water solubility. Examples of such compounds include organic molecules which lack groups that may support a formal charge (e.g., carboxylic acid and amino groups) or which lack polar groups such as hydroxyl groups. Such compounds may be amino acid-based (i.e., amino acids, peptides, polypeptide and proteins), wherein the amino acids are exclusively or predominantly hydrophobic (e.g., leucine, valine, etc.). A variety of useful or potentially useful compounds are hydrophobic. Such compounds may be useful for diagnostic, therapeutic, or other purposes, in a variety of fields such as oncology, gene therapy, cardiovascular diseases, dermatology and antibiotic therapy. Examples of specific types of uses for hydrophobic compounds include as an anesthetic, antibiotic, antifungal, antineoplastic, chemoprophylactic, immunosuppressant, glucocorticoid, nutritional supplement, photosensitizer, sunscreen, tranquilizer, vaccine, or vasodilator. Table 1 lists examples of hydrophobic compounds.

TABLE I

| | |
|---|---|
| Anesthetics | propanidid, propofol, alphadione |
| Antibiotic | echinomycin |
| Antifungal | miconazole nitrate |
| Antineoplastic | teniposide, didemnin B, taxol |
| Chemoprophylactic | praziquantel |
| Immunosuppressants | cyclosporin, cyclosporin A, 18-hydroxydeoxycorticosterone, rapamycin |
| Glucocorticoid | prednisolone |
| Nutritional supplements | Vitamin A, vitamin E, amino acids |
| Photosensitizers | purpurin, tin etiopurpurin, porphyrins |
| Sunscreens | Paraaminobenzoic acid, |
| Tranquilizer | diazepam, delta 9-tetrahydrocannabinol |
| Vaccines | BBB-MDP |
| Vasodilator | verapamil, nifedipine |

It will be evident to those of ordinary skill in the art that more than one type of hydrophobic compound may be incorporated into an oil-based mixture of the present invention.

In addition to an oil, a PEG-linked lipid and a hydrophobic compound, it may be desirable to include other molecules in the mixture. For example, in a preferred embodiment, a phospholipid is present. Phosphatidylcholine (e.g., from egg) is particularly preferred. The presence of a phospholipid appears to facilitate hydration of the oil and PEG-linked lipid, and to aid in the coating process whereby the mixture is surrounded by a lipid monolayer.

A mixture that includes the above-identified components is typically prepared within the present invention as a gel prior to emulsification in the presence of lipids. Briefly, a hydrophobic compound of choice is dissolved in an organic solvent, along with an oil and a PEG-linked lipid, to form a mixture. Suitable organic solvents include chloroform, hexane, benzene and methanol. The mixture is dried, for example, under nitrogen gas, and then evacuated for over three hours to yield a translucent gel. Alternatively, the mixture may also be dried on the inside of a test tube or other glassware, or rotary vortexed to the desired dryness. The gel is hydrated in a buffered solution (e.g., HEPES buffer and NaCl, pH 7.4), and subsequently combined with polar lipids to surround the oil-based mixture with a monolayer.

Polar lipids may be prepared for use with an oil gel by, for example, extruding a polar lipid (e.g., phosphatidylcholine) ten times through two 0.05 μm filters. This provides the essential lipid layer which coats the oil droplets and prevents them from fusing. The lipids which may be employed in the present invention include a glycolipid or a phospholipid, alone or in combination. Suitable phospholipids include phosphatidylcholine (PC), phosphatidylethanolamine (PE), phosphatidylserine (PS), phosphatidylinositol (PI), phosphatidylglycerol, phosphatidic acid, sphingomyelin (SPM) and the like. The lipids can be synthetic or derived from natural sources such as egg or soy. Steroids such as cholesterol, PEG cholesterol, coprostanol, cholestanol, cholestane, cholestano, cholesterol hemisuccinate, and organic acid derivatives of tocopherols, may be combined with the lipids. The lipids employed are chosen for optimal biodistribution and stability in circulation. In a preferred embodiment, the monolayer consists of 55%–100%, by molarity, of a phospholipid. In another preferred embodiment, the monolayer consists of 0% to 45%, by molarity, of a steroid.

If desired, the volume of a lipid-compound gel mixture can be increased with buffer or saline, and the whole is placed in a microemulsifier for an appropriate number of "strokes" at an appropriate pressure to yield particles of about 100 nanometers in diameter. Different microemulsifiers and volumes require a different number of strokes to achieve an equivalent result. Alternate means of generating the particles from a lipid-compound gel mixture are vortexing and sonication. In general, a microemulsion of the present invention has a size range of about 30 nm to 1000 nm.

It may be desirable to include a targeting moiety with a composition of the present invention. Examples of targeting moieties include biotin, avidin, streptavidin, and antibodies. As used herein, the term "antibody" includes an intact molecule, a fragment thereof, or a functional equivalent thereof. Examples of antibody fragments include antigen-binding portions, such as Fab, Fab' and F(ab')$_2$.

A variety of antibodies are commercially available. Alternatively, polyclonal or monoclonal antibodies (MAbs) which are capable of specifically binding (i.e., with a binding affinity of about $10^6$ liters per mole) a substance may be produced. Briefly, polyclonal antibodies may be produced by immunization of an animal with a substance and subsequent collection of its sera. Immunization is accomplished, for example, by systemic administration, such as by subcutaneous, intraplenic or intramuscular injection, into a rabbit, rat or mouse. It is generally preferred to follow the initial immunization with one or more booster immunizations prior to sera collection. Such methodology is well known and described in a number of references. MAbs may be generally produced by the method of Kohler and Milstein (*Nature* 256:495–497, 1975; *Eur. J. Immunol.* 6:511–519, 1976). Briefly, cells of lymph nodes and/or spleens of an animal immunized with a substance are fused with myeloma cells to form hybrid cell lines ("hybridomas" or "clones"). Each hybridoma secretes a single type of immunoglobulin specific for the substance, and, like the myeloma cells, has the potential for indefinite cell division. Suitable MAbs include those of murine or human origin, or chimeric antibodies such as those which combine portions of both human and murine antibodies (i.e., antigen binding region of murine antibody plus constant regions of human antibody). Human and chimetic antibodies may be produced using methods well known by those skilled in the art. An alternative to the production of MAbs via hybridomas is the creation of MAb expression libraries using bacteriophage and bacteria (e.g., Sastry et al., *Proc. Natl. Acad Sci.* USA 86:5728–5732, 1989; Huse et al., *Science* 246:1275– 1281, 1989).

A targeting moiety may be covalently or noncovalently associated with a lipid monolayer of a composition of the present invention. For example, activated lipids are commercially available (e.g., Avanti Polar Lipids, Inc.) which possess chemically reactive groups for covalently joining a targeting moiety. Typically, a targeting moiety is reacted via one of the nucleophilic groups (e.g., amino or sulfhydryl) with a chemically reactive group on an activated lipid. Chemically reactive groups include, for example, iodoacetyl, maleimidylbenzoyl, maleimidylphenyl, and pyridyldithio groups. Methodologies for the preparation of targeting moieties associated with lipids are well known to those of ordinary skill in the art (see, for example, *Liposome Technology*, Vol. III, G. Gregoriadis, ed., CRC Press, Inc., Boca Raton, Fla.; Loughrey et al.; *Biochim. Biophys. Acta* 901:157, 1987; Loughrey et al., *J. Immunol. Methods* 132:25, 1990). In addition, certain lipids already possessing a targeting moiety are commercially available, e.g., biotinoyl phosphoethanolamines. It will be appreciated by those of ordinary skill in the art that a wide variety of targeting moieties may be associated with lipids for use in a composition of the present invention.

The compositions of the present invention have a variety of in vitro and in vivo uses. In one aspect, such compositions may be used in a method for delivering a hydrophobic compound to cells in vitro. In one embodiment, cells are contacted with a composition of the present invention under conditions and for a time sufficient to permit delivery of a hydrophobic compound to the cells. Typically, cultured cells are incubated with a composition at 37° C. for a time ranging from about 24 h to 72 h. Such a method is useful to determine what affect, if any, a particular hydrophobic compound has upon a particular cell type. A compound may, for example, inhibit or enhance the growth of cells exposed to the compound via a composition of the present invention. For example, a method of the present invention may be used for in vitro cytotoxicity studies to test the ability of a hydrophobic compound to function as a cell growth inhibitor. Such a method is particularly useful to test the ability of hydrophobic compounds to kill or inhibit the growth of tumor cells.

In another aspect, the compositions of the present invention may be used in a method for delivering a hydrophobic compound to cells in vivo. In one embodiment, a composition of the present invention is administered to a warm-blooded animal, including mammals such as humans, under conditions sufficient to permit delivery. It will be appreciated by those of ordinary skill in the art that the amount of a composition administered will depend upon the particular hydrophobic compound utilized and the result to be effected. Prior to administration, a composition may be combined with a pharmaceutically acceptable carrier or diluent. Pharmaceutically acceptable carriers and diluents include water, physiological saline, alcohols, and mixtures thereof. A composition may be administered by a variety of routes, including parenteral, topical and oral. For administration by injection, physiological saline is a preferred diluent.

The following examples are offered by way of illustration and not by way of limitation.

EXAMPLES

EXAMPLE 1

Synthesis of PEG-linked Lipids

Abbreviations:

| | |
|---|---|
| MePEGS | monomethoxypolyethylene glycol succinate |
| MePEGC | monomethoxypolyethylene glycol carbonate (when attached to PE) |
| MePEGA | (monomethoxypolyethylene glycol) acetic acid |
| MePEG-OH | monomethoxypolyethylene glycol |
| MePEGC-2000-Cl | monomethoxypolyethylene glycol$_{2000}$ chloroformate |
| MePEG3-2000 | monomethoxypolyethylene glycol$_{2000}$ succinate |
| MePEG-2000-OH | monomethoxypolyethylene$_{2000}$ glycol |
| MePEGA | (monomethoxypolyethylene glycol$_{2000}$) acetic acid |
| DCC | dicyclohexylcarbodiimide |
| NHS | N-hydroxy succinimide |

A. General Procedures for synthesis of PEGylated lipids

1. MePEGS-xxPE

Dry MePEGS (1.1 equiv.), DCC (1.2 equiv.) and NHS (1.7 equiv.) were dissolved in chloroform and stirred at room temperature for one hour. The solution was filtered and treated with dry xxPE (1.0 equiv.). Triethylamine (10 equiv.) was added and the reaction mixture stirred at room temperature for half an hour. The solution was diluted with water, acidified with dilute hydrochloric acid and extracted with chloroform (3x). The combined organic extracts were dried over magnesium sulphate, filtered and the solvent removed. The residue was subjected to column chromatography. Fractions containing MePEGS-xxPE were combined and the solvent removed. The residue was dispersed in water, dialysed against distilled water for eight hours and lyophilised.

2. MePEGG-xxPE

Dry MePEG-OH (1.1 equiv.) was dissolved in chloroform/toluene (50:2) and treated with triphosgene (3.3 equiv.) with stirring at room temperature in a sealed flask for two days. Most of the solvent was removed under reduced pressure. Ether was then added to precipitate the product. The precipitate was filtered, washed with ether and dried on a lyophiliser. The product was dissolved in a solution of xxPE (1 equiv.) in chloroform, treated with triethylamine (10 equiv.) and allowed to stand at room temperature for an hour. The reaction mixture was then worked up as in 1.

3. MePEGA-xxPE

Dry MePEGA (1.1 equiv.), DCC (1.2 equiv.) and NHS (1.7 equiv.) were dissolved in chloroform and stirred at room temperature for one hour. The solution was filtered and treated with dry xxPE (1.0 equiv.). Triethylamine (10 equiv.) was added and the reaction mixture stirred at room temperature for half an hour. The reaction mixture was then worked up as in 1.

4. MePEG-xxPA

A mixture of xxPA (1.0 equiv.), MePEG-OH (1.1 equiv.) and triisopropylbenzenesulphonyl chloride (7 equiv.) was suspended in pyridine. The reaction mixture was protected from light and allowed to stir at room temperature overnight. Water was added and the mixture allowed to stir for a further three hours. The reaction mixture was then worked up as in 1.

B. Procedures for synthesis of PEGylated PO-lipids

1. MePEGG-2000-POPE

Dry MePEGS-2000 (0.57 g), DCC (0.19 g) and NHS (0.12 g) were stirred at room temperature for an hour. The solution was filtered and the filtrate treated with dry POPE (0.50 g) and triethylamine (1 ml) at room temperature, with stirring, for half an hour. The reaction mixture was diluted with water, acidified and extracted with methylene chloride (3×20 ml). The organic extracts were dried over magnesium sulphate, filtered and the solvent removed. The residue was dissolved in a minimum of methylene chloride and precipitated with ether. The filtered precipitate was dried, dispersed in water, centrifuged and the decanted solution lyophilised. The resultant powder was subjected to column chromatography using silica gel and methanol/methylene chloride. Pure fractions were combined, the solvent removed and the residue taken up in water. The solution was centrifuged and the supernatant dialysed for seven hours. The dialysed solution was lyoplfilised to yield a white powder (0.75 g).

2. MePEGC-2000-POPE

Drt MePEG-2000-OH (2 g) was dissolved in chloroform/toluene (60 ml/2 ml) and treated with triphosgene (0.95 g) with stiffing at room temperature for two days in a sealed flask. Most of the solvent was removed under reduced pressure and the product precipitated by addition of ether. The precipitate, MePEGC-2000-Cl (2 g), was filtered and dried under vacuum. MePEGC-2000-Cl (0.9g) and dry POPE (0.225 g) were dissolved in chloroform (5 ml), treated with triethylamine (0.1 ml) and allowed to stand at room temperature for half an hour. More MePEGC-2000-Cl (0.2 g) and triethylamine (0.5 ml) were added and the reaction mixture allowed to stand for half an hour. The solvent was removed under vacuum and the residue dissolved in water. The aqueous solution was acidified and extracted with methylene chloride (3×20 ml). The combined organic fractions were dried over magnesium sulphate, filtered and the solvent removed. The residue was subjected to column chromatography using silica gel and methanol/methylene chloride. The combined dried fractions containing pure MePEGC-2000-POPE were dispersed in water, centrifuged at 3000 rpm for half an hour and the supernatant lyophilised to yield a white powder (0.2 g).

3. MePEGA-2000-POPE

MePEG-2000-OH (5.11 g) was added to a solution of sodium dichromate (3.10 g) in dilute sulphuric acid (100 ml, 10%) and the solution stirred at room temperature overnight. The solution was extracted with methylene chloride (3×20 ml) and the combined organic extracts washed with dilute sodium hydroxide solution (1M). The organic fraction was dried over magnesium sulphate, filtered and the solvent removed under reduced pressure. The residue was dissolved in a minimum of chloroform and precipitated with ether. The precipitate was filtered and dried, yielding MePEGA-2000 as a pale blue powder (3 g; color due to residual complexed chromium). A mixture of crude MePEGA-2000 (3 g), DCC (120 rag) and HNS (100 rag) in methylene chloride was stirred for two hours and filtered. POPE (0.4 g) was added to the filtrate, followed by triethylamine (0.3 ml), and the reaction mixture stirred at room temperature overnight. The reaction mixture was diluted with water; acidified with dilute hydrochloric acid and extracted with methylene chloride (3×20 ml). The combined organic fractions were dried over magnesium sulphate. filtered and the solvent removed. The residue was dissolved in a minimum of chloroform, precipitated with ether and filtered. The precipitate was dried, dispersed in a minimum of water, centrifuged at 3000 rpm for half an hour and dialysed against distilled water for twenty-four hours. Lyophilisation of the aqueous solution yielded MePEGA-2000-POPE, still contaminated with some MePEGA-2000, as a white powder (0.92 g). Column chromatography yielded pure MePEGA-2000-POPE (0.32 g).

4. MePEG-2000-POPA

A mixture of POPA (0.15 g), MePEG-2000-OH (0.57 g) and triisopropylbenzenesulphonyl chloride (0.50 g) was suspended in pyridine (5 ml). The reaction mixture was protected from light and allowed to stir overnight. Water was added and the mixture allowed to stir for a further three hours. The solutions was diluted with water, acidified and extracted with methylene chloride (2×). The residue was dispersed in water, filtered, centrifuged and the supernatant lyophilised. The resultant powder was subjected to column chromatography using silica gel and methanol/chloroform. The purest fractions were combined and dialysed as usual to yield a white powder (0.27 g). Less pure fraction (157 rag) was dialysed to yield (80 mg). Two components were combined to yield 0.35 g for CC. The mixture was subjected to CC using silica gel and methanol/methylene chloride. Pure fractions were combined, taken up in water, centrifuged and lyophilised to yield a white powder (0.18 g).

EXAMPLE 2

Preparation of Unloaded Microemulsions

Figure 1:
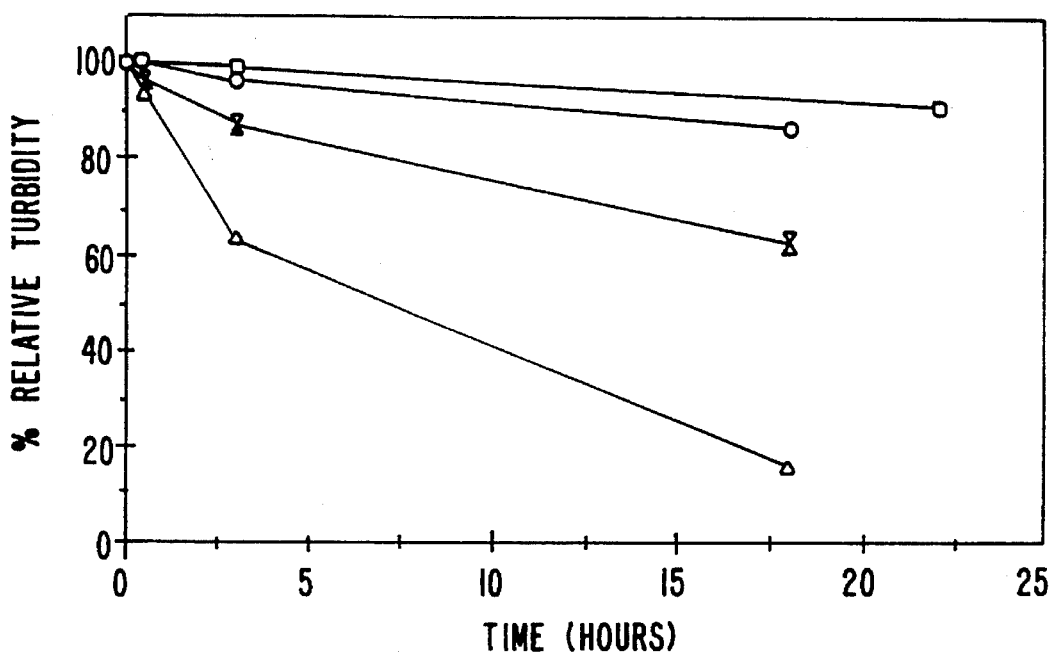
FIG. 1 graphically illustrates the stability of oil emulsions coated with MePEGS-5000-POPE. Corn oil (15 gm) was hydrated in 1 ml HBSS and sonicated. Where phospholipid was present, EPC and the indicated concentration of MePEGS-5000-POPE (mol:mol) was dried under $N_2$ to a thin film from $CHCl_1$. The hydrated oil was added directly to the thin phospholipid film, vortexed and sonicated. The turbidity of an appropriately diluted suspension was measured on a spectrophotometer at 640 nm. The percent relative turbidity was calculated as the ratio of the absorbance at any given time over the absorbance at time 0. ∆ no phospholipid; ✕ 0% MePEGS-5000-POPE; ◯ 1% MePEGS-5000POPE; and ☐ 5% MePEGS-5000-POPE.

Corn oil (15 mg) (U.S. Biochemical Corp., Cleveland, Ohio) was hydrated in 1 ml HEPES Buffered Saline Solution ("HBSS") (20 mM HEPES+150 mM NaCl, pH 7.4) and sonicated. Egg phosphatidylcholine ("EPC") (Avanti Polar Lipids, Inc.) and the indicated concentration (Table 2) of the MePEGS-5000-palmitoyl oleoyl phosphatidylethanolamine ("MePEGS-5000-POPE") or MePEGS-2000-distearoyl phosphatidylethanolamine ("MePEGS-2000 DSPE") (mol:mol; Example 1 or Avanti Polar Lipids, Inc., Alabaster, Ala.) was dried from $CHCl_3$ under $N_2$ to a thin film. The hydrated corn oil was added directly to the thin phospholipid film, and then the whole was vortexed and sonicated (using a Branson Sottic Power Sonifier Model 350) until the particles were approximately 100 nm in diameter (three 15-second periods). The turbidity of an appropriately diluted suspension was measured on a spectrophotometer at 600 nm. The percent relative turbidity was calculated as the ratio of the absorbance at any given time over the absorbance directly after preparation. Results are shown in FIGS. 1 and 2. The addition of either MePEGS-5000-POPE or MePEGS-2000-DSPE substantially reduces the size of the particles and increases stability over phospholipid-free oil emulsions.

TABLE 2

| Formula | Amount in milligrams if not otherwise marked |
| --- | --- |
| corn oil | 15 |
| HBSS | 1 Ml |
| Me PEG S 2000 DSPE or Me PEG S 5000 | 1.6 |

TABLE 2-continued

| Formula | Amount in milligrams if not otherwise marked |
|---|---|
| POPE | |
| EPC | 3.8 |

EXAMPLE 3

Preparation of Taxol Emulsions

A taxol formulation was prepared by adding 10 mg taxol (Napro Inc., Boulder, Colo.) to 150 mg corn oil. Subsequently a mixture of 20 mg MePEGS-2000-DSPE and 40 mg EPC in $CHCl_3$ were added. The $CHCl_3$ is removed under a stream of $N_2$ followed by vacuum evaporation for at least 4 hours. The resulting taxol-containing lipid was clear. The film was hydrated by the addition of 2 ml of HBSS followed by addition of 2 ml of EPC phospholipid donating vesicles 70 nm in diameter. The above mixture was therefore 1 mg/ml and the taxol to corn oil ratio was 1 to 15. The mixture was passed through the Microfluidizer microemulsifier (M-S model distributed by Microfluidics Corporation, Newton, Mass.) at an operating pressure of 70–75 psi. Approximately four strokes of the piston correspond to one pass of 10 ml though the mixing chamber. The emulsion became translucent after approximately 20 strokes or 5 passes.

Figure 4:
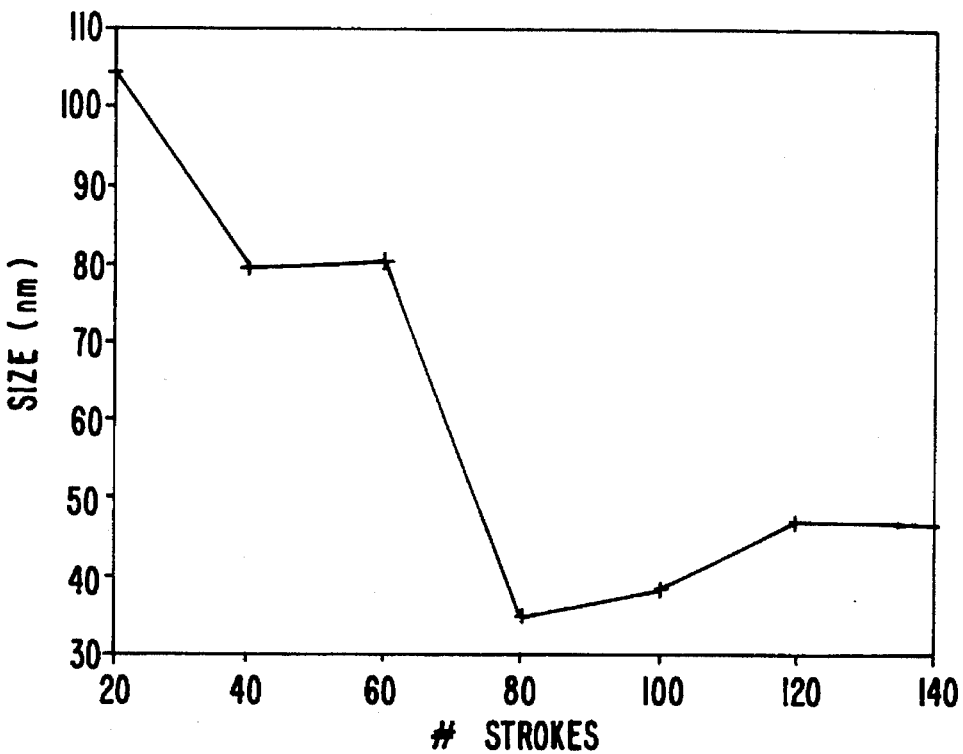
FIG. 4 graphically illustrates the effect of number of strokes on the size of emulsions produced by the microfluidizer. Taxol (10 mg) was added to 150 mg corn oil followed by the addition of 40 mg EPC and 20 mg MePEGS-2000-DSPE in $CHCl_3$. All components are readily soluble in $CHCl_3$. $CHCl_3$ was removed under $N_2$ followed by 4 hours of vacuum evaporation. The resulting film was hydrated in 2 ml HBSS. To this was added 2 ml of 150 mg of EPC vesicles which had been extruded through two stacked 0.05 um polycarbonate filters. The mixture was brought to 10 ml with HBSS and processed in the microfluidizer.

As shown in FIG. 4, the size of the oil droplets decreased with each pass through the Microfluidizer. After about 80 to 100 strokes a the minimum size is achieved, and further processing only caused the particles to aggregate and congeal.

This phenomenon is also observed when the emulsion is sonicated extensively or extruded through polycarbonate filters of small (<100 nm) pore size.

All studies describing the characteristics of the taxol particles use emulsions which exhibit a mean particle size (as judged by Quasielastic light scattering (QELS) data indicated in FIG. 4) of less than 100 mn.

EXAMPLE 4

Size Analysis of Emulsions With Taxol or Without Taxol

Emulsions were prepared as in Examples 2 and 3, and were sonicated. The size distributions were immediately analyzed on a Nicomp Model 270 Submicron Particle Sizer. The 10% MePEGS-2000-DSPE and taxol sample contained 0.5 mg/ml of taxol. As the percentage MePEGS-2000-DSPE increased, the size of the particles decreased. The addition of taxol prompted a further reduction in particle size.

EXAMPLE 5

Effect of Microfluidizer Stroke Number on Emulsion Size

Taxol (10 mg) was added to 150 mg corn oil followed by the addition of 40 mg EPC and 20 mg MePEGS-2000-DSPE in $CHCl_3$. All components are readily soluble in $CHCl_3$. $CHCl_3$ was removed under $N_2$ followed by 4 hours of vacuum evaporation. The resulting film was hydrated in 2 ml HBSS. To this, 2 ml of 150 mg of EPC vesicles which had been extruded through two stacked 0.05 micrometer polycarbonate filters were added. The mixture was brought up to 10 ml with HBSS and processed in the Microfluidizer.

EXAMPLE 6

Freeze Fracture Electromicroscopy

Particles containing a concentration of 0.5 mg/ml taxol were prepared by sonication. A 100 µl aliquot of the sample was frozen in liquid freon and freeze etched in a Baizers Freeze-Etching System BAF 400D (Balzers Machine, Balzer, Liechtenstein). The samples were etched prior to preparation of the replica which is then viewed by electromicroscopy. The samples were cryofixed in the presence of 25% glycerol by plunging into liquid freon 22. Systems were etched for 1minute at 183K after fracturing at 163K (10–6 to 10– 7 torr). The fractured surface was shadowed unidirectionally with platinum and coated with carbon. Etching involves a process whereby the samples are warmed slightly for one to two minutes to allow sublimation of the frozen water in the freeze-fracture apparatus. The micrographs were obtained using a JEOL Model JEM-1200 EX Electron Microscope. Since the oil does not sublimate, the resulting replica give the appearance of smooth regions surrounded by rougher areas where sublimation occurred.

EXAMPLE 7

$^{31}$P-NMR Spectra

Figure 3:
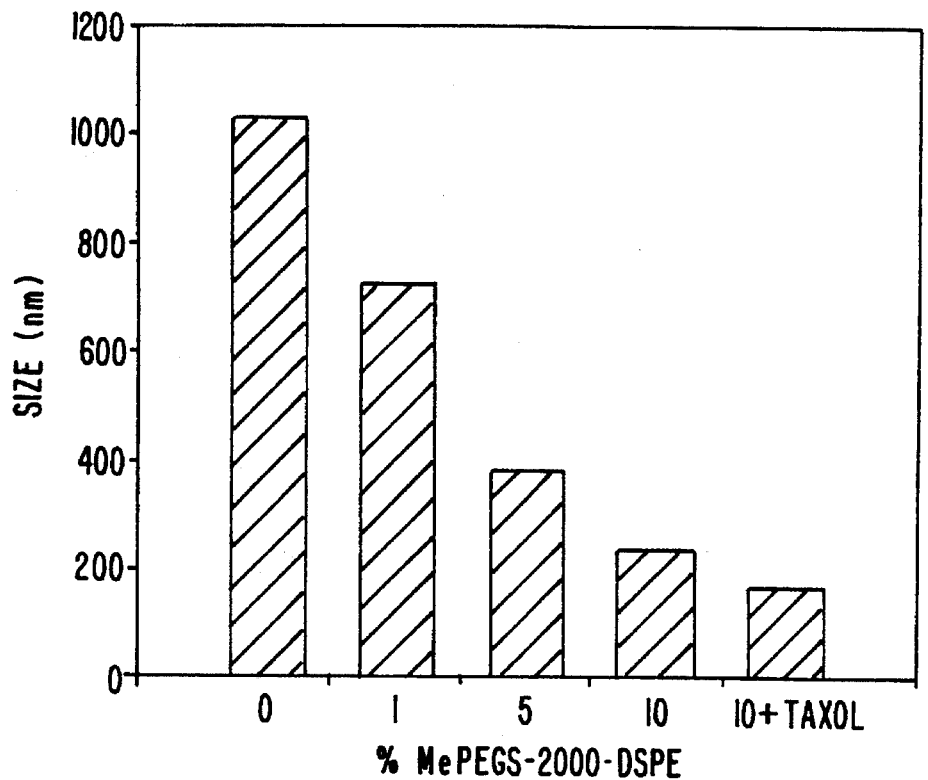
FIG. 3 graphically shows the size distribution of emulsions. Emulsions prepared as in FIG. 1 were sonicated and the size distributions were immediately analyzed on a Nicomp Submicron Particle Sizer. The 10% MePEG-2000-DSPE+taxol sample contained 0.5 gm taxol/ml.

NMR was generally performed according to the methods described in Wong et al., *Biochim. Biophys.* Acta 921:411–414, 1987 (see FIG. 3 therein). To show the effect of $Mn^{2+}$ quenching, proton decoupled P31 NMR spectra (81.0 MHz) were obtained with MnCI added at 5 mmol.

Figure 6:
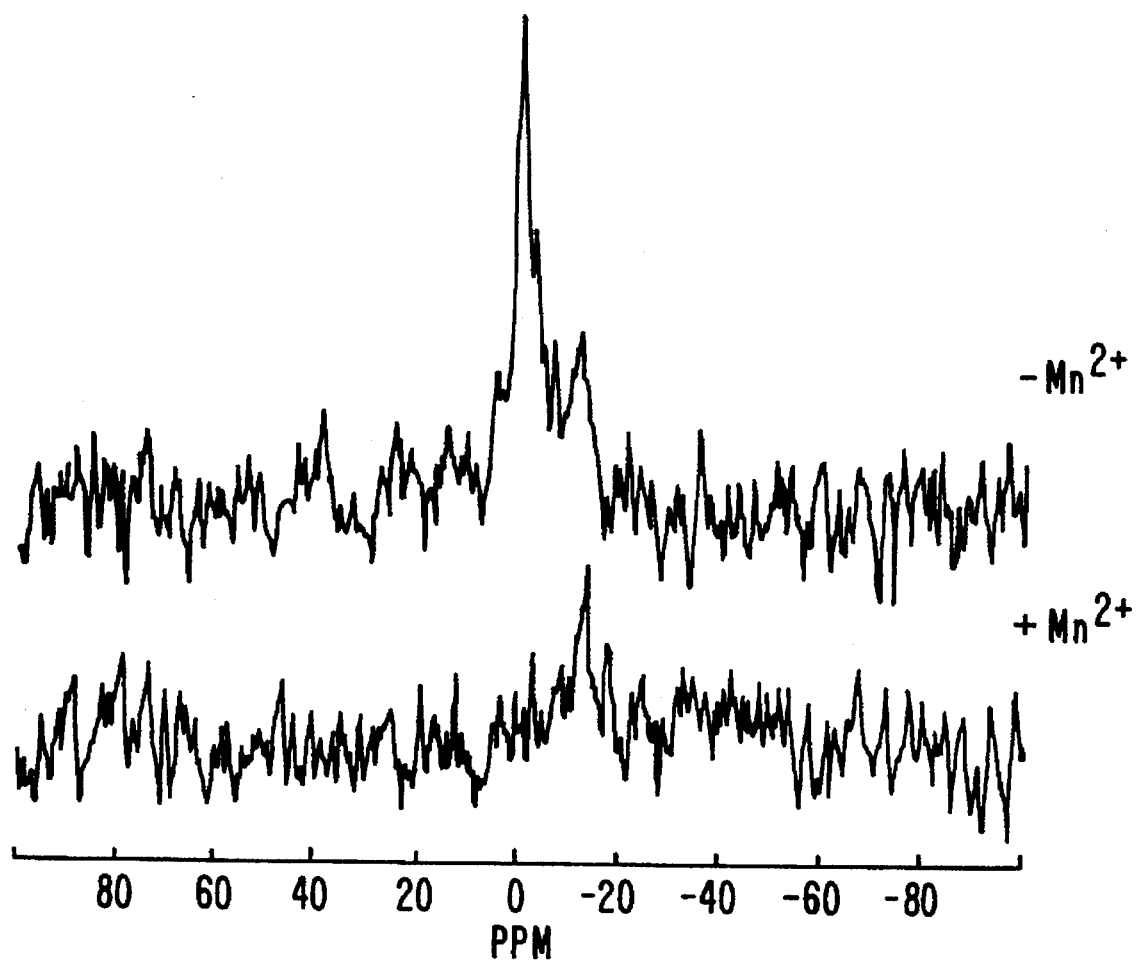
FIG. 6 shows a proton-decoupled $^{31}$P NMR spectra (81.0 MHz) of the same sample as in FIG. 5. The upper trace is in the absence of $Mn^{2+}$ while the lower trace is in the presence of 5 mM $Mn^{2+}$ (as $MnCl_2$). More than 70% of the phospholipid is quienced in the presence of 5 mM $Mn^{2+}$ indicating that the majority of the phospholipid is present as a monolayer surrounding the oil droplets. The small peak which remains in the lower trace is probably due to trace phospholipid contaminants in the oil. Such contaminants are known to occur.

$^b$ $^{31}$P-NMR of studies indicates these oil droplets are coated with a monolayer of EPC and PEG-modified phospholipids. These studies involve addition of the broadening reagent, $Mn^{2+}$, to the sample. $Mn^{2+}$ binds the phosphate in the phospholipid head group and the resulting $^{31}$P-NMR signal broadens. If such a study is completed using unilamellar liposomes, only 50% of the phospholipid is available to $Mn^{2+}$ and one sees a 50% reduction in signal i. As shown in FIG. 6, $Mn^{2+}$ addition to taxol particles results in a 100% reduction in the $^{31}$P-NMR signal, indicating that the phospholipid was organized as a monolayer.

Figure 5:
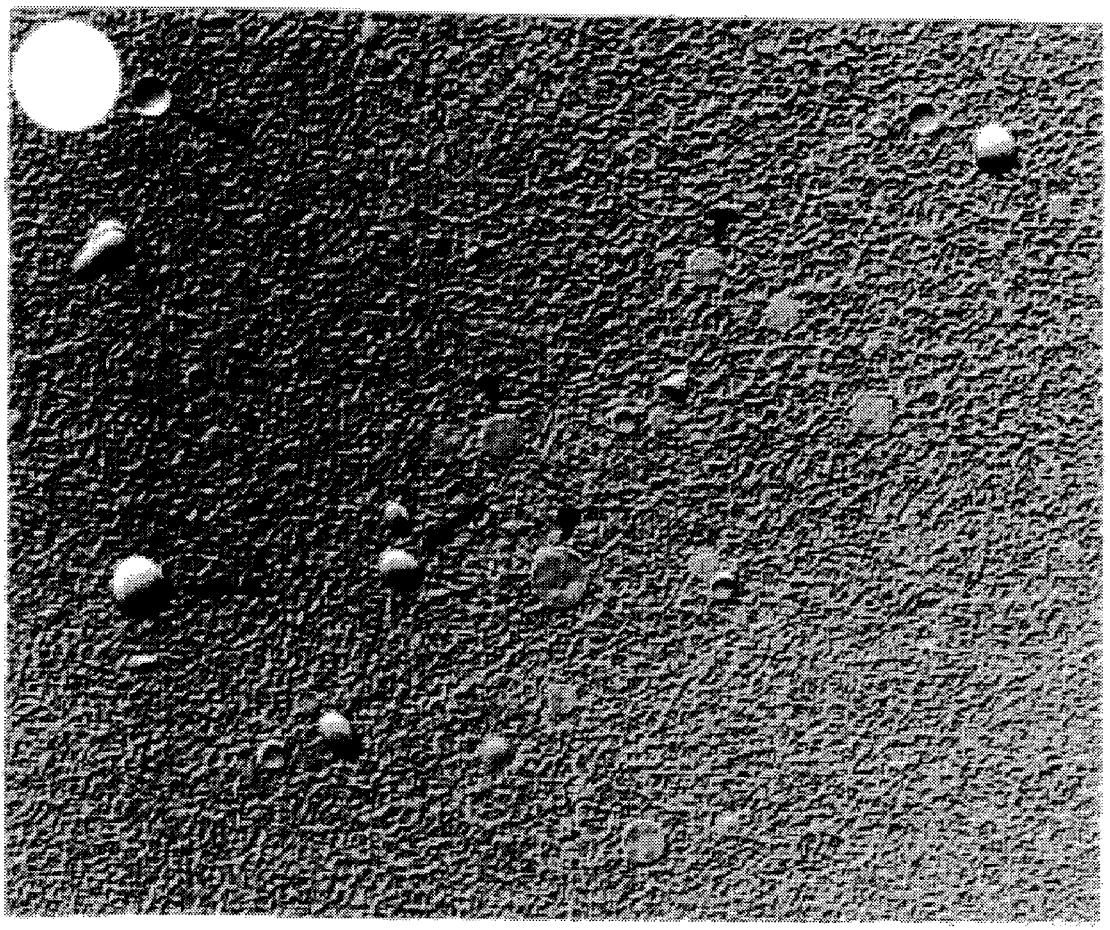
FIG. 5 pictorially depicts freeze-fracture electron microscopy of a sonicated preparation of taxol in corn oil. Sonicated oil emulsions containing taxol (0.5 mg/ml) were prepared as described in FIG. 1. A 100 μm aliquot of the sample was frozen in liquid freon and freeze-etched in a Baizers Freeze-Etching System BAF 4001. The micrographs were obtained using a JEOL Model JEM-1200 EX Electron Microscope. The samples were cryofixed in the presence of 25% glycerol by plunging into liquid freon 22. Systems were etched for 1 min at 183K after fracturing at 183K ($10^{-6}$-$10^{-7}$ torr). The fractured surface was shadowed unidirectionally.

Proton decoupled $^{31}$P-NMR spectra (81.0 MHz) of the same sample as in FIG. 5. The upper trace is in the absence of $Mn^{2+}$ (as $MnCl_2$). More than 70% of the phospholipid is quenched in the presence of 5 mM $Mn^{2+}$, indicating that the majority of the phospholipid is present as a monolayer surrounding the oil droplets. The small peak which remains in the lower trace is probably due to trace phospholipid contaminants in the oil, which are known to occur.

EXAMPLE 8

Column Chromatography

Figure 7A:
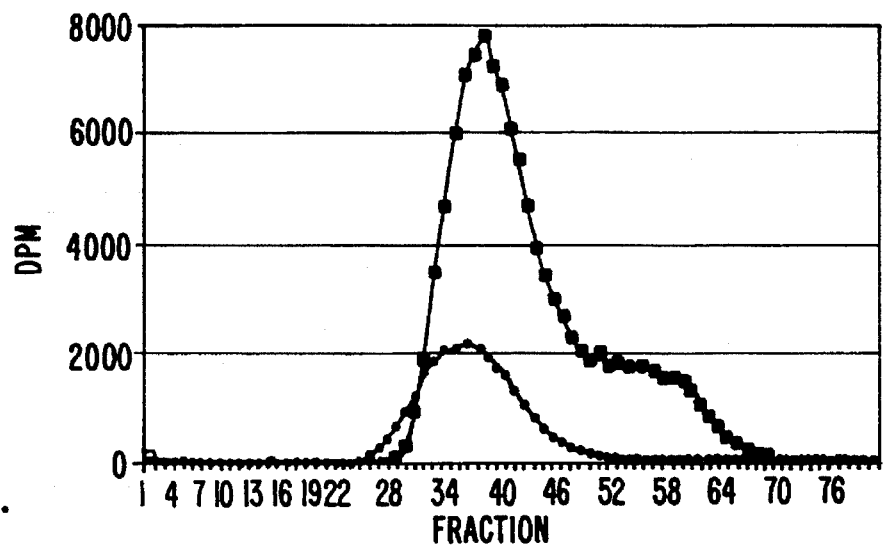
FIG. 7 graphically illustrates an elution profile of Bristol-Meyers Squibb (BMS) taxol (Panel A) and taxol particles of the present invention (Panel B). A 100 μaliquot containing 1 mg taxol/ml was added to 500 μl of HBSS and 500 μl of this was eluted on a 10 ml Sepharose CL-4B column in HBSS. Fraction volumes were 0.5 ml. [$^3$H] taxol and [$^{14}$C] cholesteryl hexadecylether (CHDE) was used as markers for taxol and lipid, respectively. For the BMS taxol preparation, the specific activities were 1392.8 dpm/ug taxol and 4.0 dpm/ug lipid. For the taxol preparation of the present invention, the specific activities were 763.7 dpm/ug taxol and 2.0 dpm/mg lipid. ■ taxol; ● CHDE.
Figure 7B:
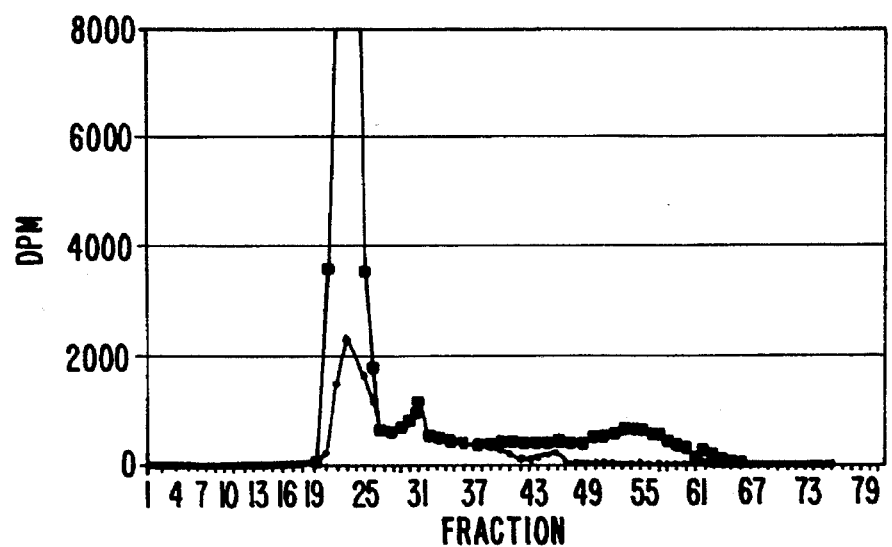
Figure 8:
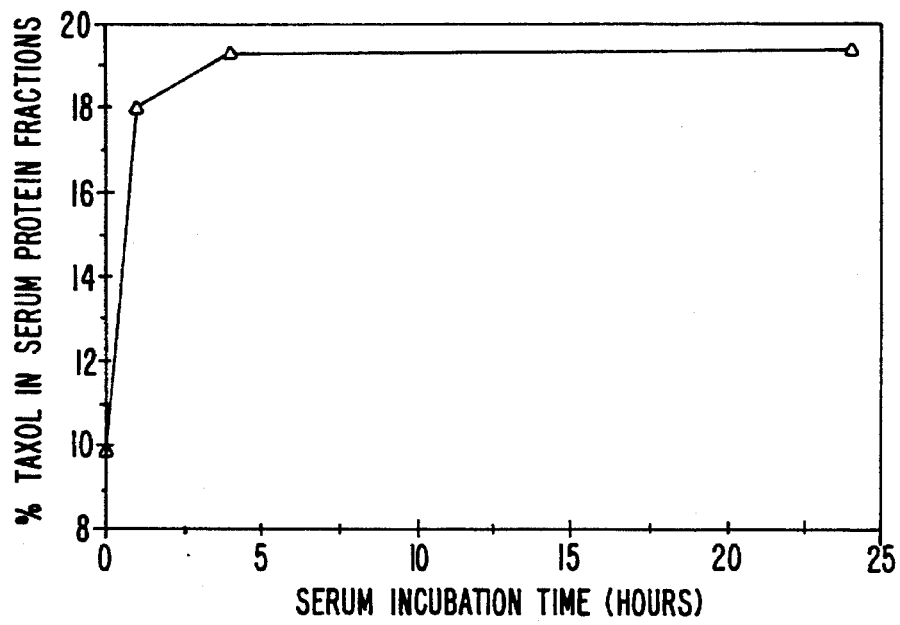
FIG. 8 graphically depicts the stability of taxol particles of the present invention in mouse serum. A 100 μl aliquot of particles (1 mg/ml) was added to 500 μl of mouse serum and incubated at 37° C. over time. A 500 μl aliquot was eluted on a 10 ml Sepharose CL-4B column in HBSS. The percent taxol recovered from the fractions corresponding to the serum proteins is plotted over time. The specific activities were as in FIG. 7.
Figure 9A:
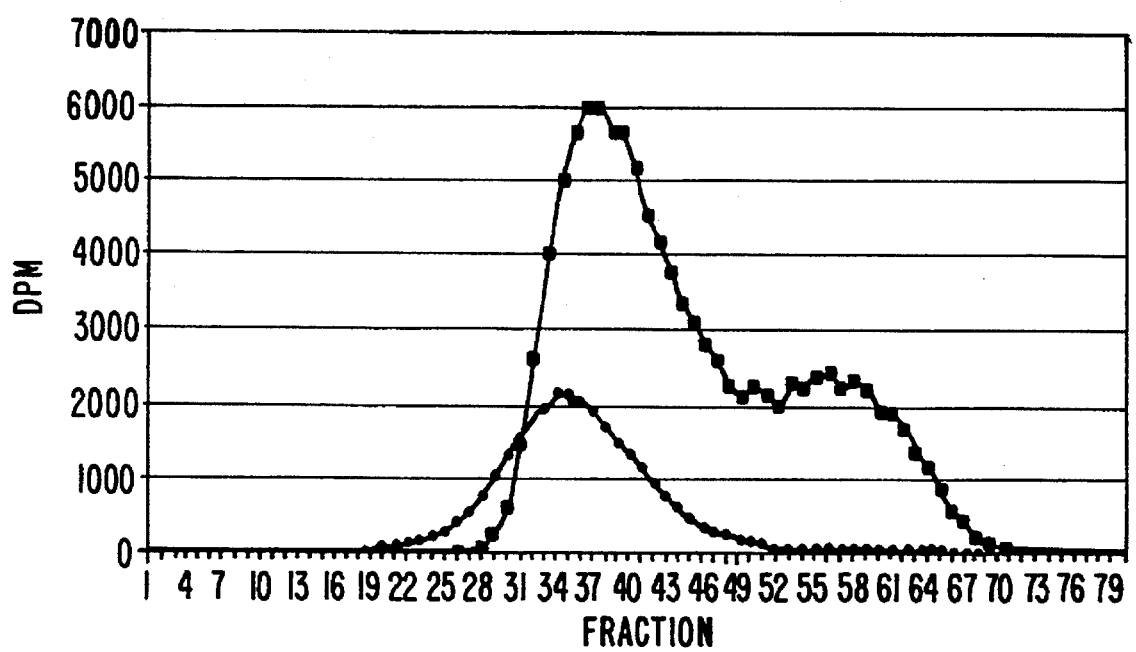
FIG. 9 is an elution profile of BMS taxol (Panel A) and taxol particles of the present invention (Panel B) after 24 hours incubation in mouse serum at 37° C. Procedures were as described for FIG. 8. ■ taxol; ● CHDE.
Figure 9B:
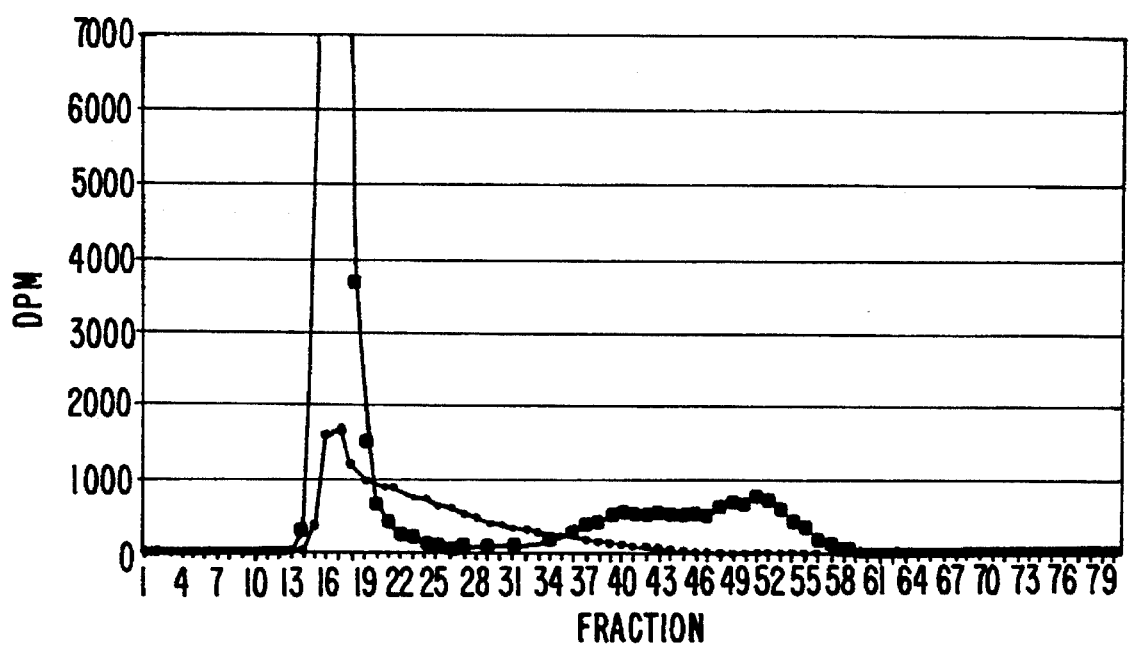
Figure 10:
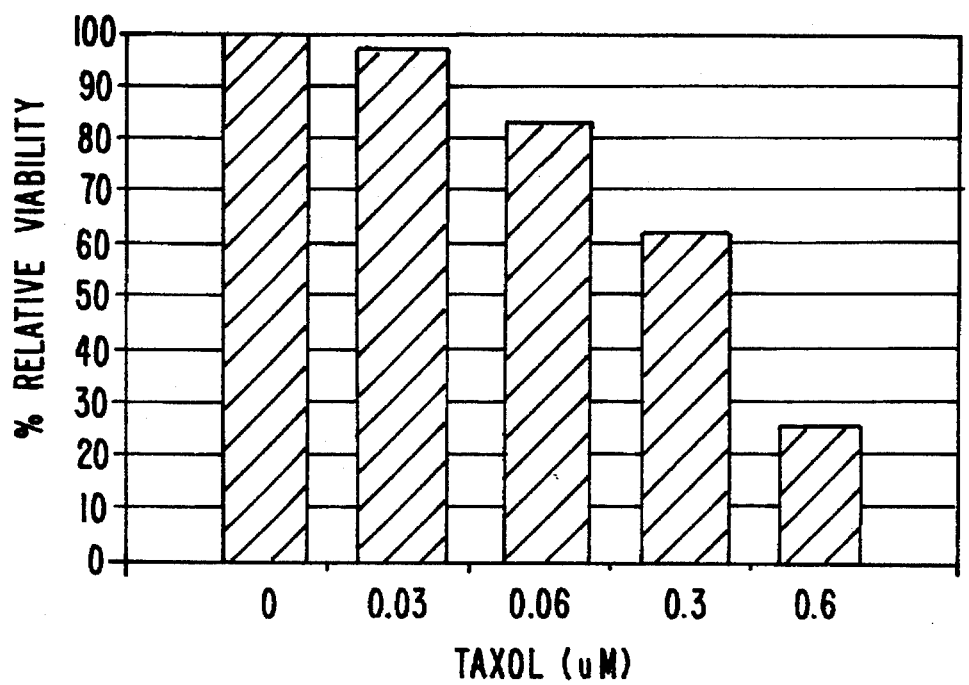
FIG. 10 graphically illustrates the cytotoxicity of taxol particles of the present invention against the murine leukemia P388 cell line. A sonicated taxol emulsion was incubated with P388 cells in 2 ml well plates for 24 hours at 37° C. Cells were harvested and counted. Nonviable cells were stained with the fluorescent nuclear stain, propidium iodide, and counted relative to live cells on a flow cytometer. The percent relative viability was calculated as the ratio of the number of live cells obtained following taxol treatment for 24 hours to the number of cells present in cultures which were not exposed to taxol.

More detailed characterization of the particles involved analysis after column chromatography. Briefly, Bristol-Meyers Squibb ("BMS") taxol and taxol particles prepared according to Example 3 were fractionated on a Sepharose® 4B CL column. These studies also incorporated a lipid marker, $^C$-cholesterol hexadecylether, because the distribution of this label should reflect the presence of the bulk of lipid in either formulations. Samples of 500 µl were added to the column and 0.5 ml fractions were collected. As shown in FIG. 7a, BMS taxol eluted as a single peak at 19 ml with a spread of 14–32 ml and with an extended shoulder (specific activity was 1392.8 dpm/μg taxol and 4.0 dpm/μg lipid). The $^{14}$C-labeled lipid eluted as a single broad peak which centered at 18 ml. In comparison, in the elution profile of taxol particles of the present invention, the taxol appeared in the void volume as a single peak with approximately 10% eluted at a volume of 26–28 ml (specific activities were 763.7 dpm/ug taxol and 2.0 dptn/ug lipid). The $^{14}$C-labeled lipid migrated as a single peak which eluted with taxol. This column chromatographic technique clearly demonstrates that the BMS formulation and the taxol particles of the present invention are different. For example, the BMS formulation is made up of smaller particles which are probably micellar.

EXAMPLE 9

In Vitro Cytotoxicity Studies

The murine leukemia P388 cell line (NCI, Bethesda, Md.) was incubated with various concentrations of taxol particles of the present invention (prepared by sonication) in 2 ml well plates for 24 h at 37° C. Cells were harvested and counted. Nonviable cells were stained with the fluorescent nuclear stain, propidium iodide, and counted relative to live cells on a flow cytometer. The formulation showed an $IC_{50}$ (the "inhibitory concentration," the concentration at which a 50% reduction in cell growth is observed) of about 0.3 μM taxol. The percent relative viability was calculated as the ratio of the number of live cells obtained following taxol treatment for 24 h to the number of cells present in cultures which were not exposed to taxol. As is typical of cell growth inhibitors, the decrease in % viable cells was due mainly to a reduction in cell number rather than cell death.

This experiment demonstrates that the compounds of the taxol particles of the present invention do not interfere with the ability of taxol to kill or inhibit the growth of tumor cells in an in vitro cytotoxicity assay.

EXAMPLE 10

In Vivo Toxicity Studies

BMS taxol or particles of the present invention were administered at 5 mg/kg via the lateral tail vein in female BDFI mice (Charles River, Trois Rivieres, Quebec) (20–22 grams in weight). The dose was selected from dose ranging experiments suggesting that 5 mg/kg was the highest dose achievable short of inducing acute toxic side effects. At 10 mg/kg, BMS taxol administration led to an acute reaction comprising convulsions followed by catatonia. These animals remained comatose for 15–30 minutes after injection. Conversely, taxol particles of the present invention were administered at doses of up to 20 mg/kg with no adverse effects.

Figure 11:
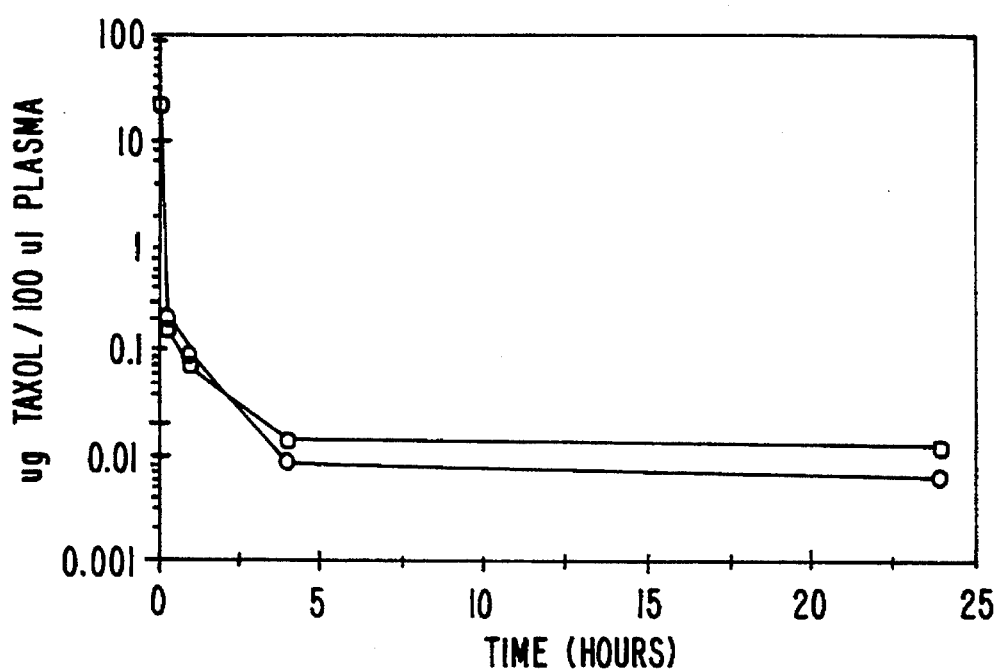
FIG. 11 graphically depicts clearance of BMS taxol and taxol particles of the present invention from plasma. BMS taxol or taxol particles of the present invention were injected into BDF1 mice via the caudal vein at a concentration of 5 mg/kg. At 15 minutes, 1 hour, 4 hours, 24 hours, three mice were sacrificed and the plasma (100 ul) was assayed for [$^3$H] taxol. The specific activities were 1608.68 dpm/ug taxol for the BMS formulation and 1241.89 dpm/ug taxol for the formulation of the present invention. □ BMS Taxol; ○ Taxol particles of the present invention.
Figure 12A:
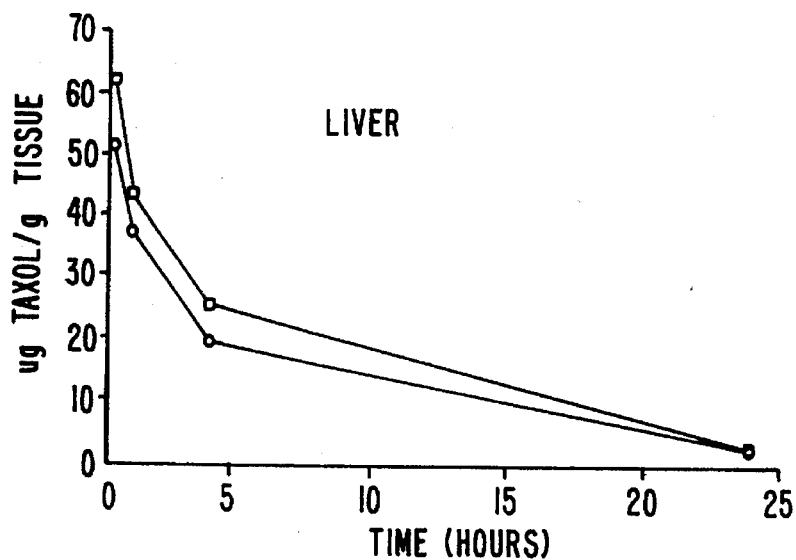
FIG. 12 graphically illustrates the distribution of taxol in liver (Panel A), spleen (Panel B), and kidney (Panel C). The livers, spleens and kidneys from the mice from FIG. 11 were assayed for [$^3$H] taxol. □ BMS Taxol; ○ Taxol particles of the present invention.
Figure 12B:
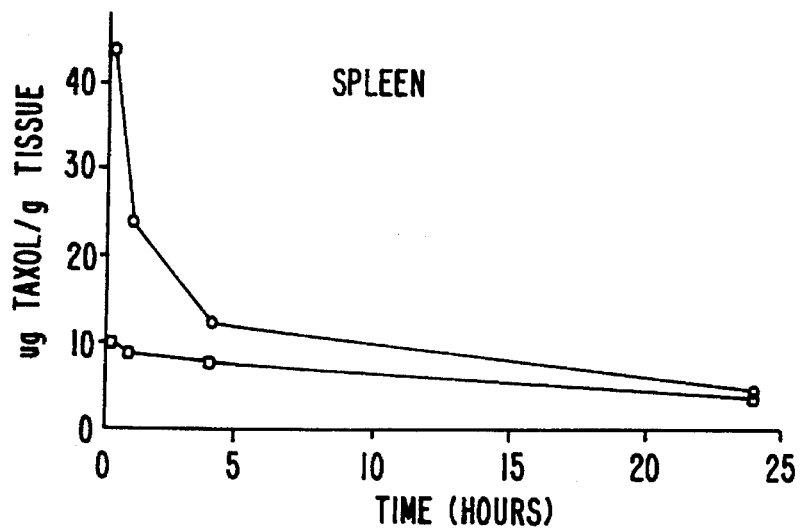
Figure 12C:
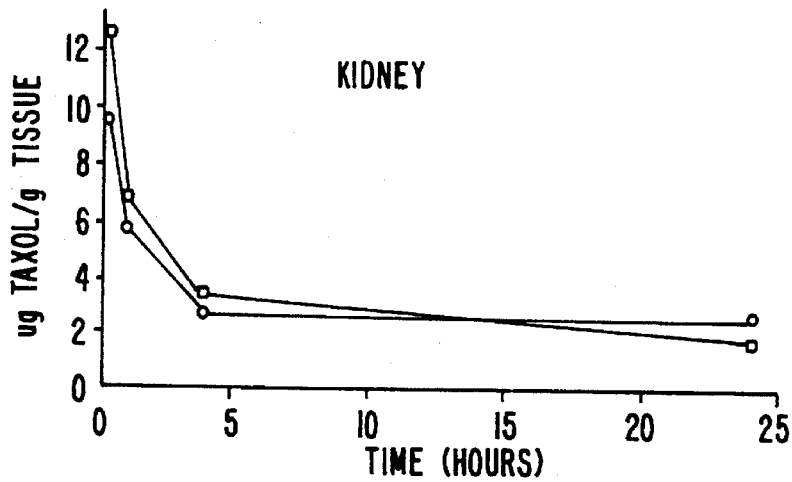

After administration of drug, animals were terminated in groups of three at post-administration times of 0.25, 1, 4, and 24 hours. Blood, liver, kidney, spleen, lung and muscle tissue samples were collected. Taxol concentration as measured by tracer quantities of radiolabeled taxol was measured in both whole blood and plasma. The results shown in FIG. 11 demonstrate that, for both formulations, taxol is cleared from circulation very rapidly. Within 15 minutes, less than 1% of the administered taxol dose remains in the plasma or whole blood compartment. At 4 hours the drug was undetectable for both formulations. Tissue distribution data for selected organs are shown in FIG. 12. The spleen was the only organ which showed significant differences of taxol concentration between the two formulations, with significantly greater drug levels following administration of taxol particles of the present invention. Other tissues samples showed that greater than 50% of the administration dose was recovered in the liver at the 15 minutes time point for both formulations. Rapid elimination from this organ was consistent with taxol's primary route of elimination though biliary excretion. Kidney levels were also significant, indicating that the drug was also removed though renal clearance.

From the foregoing, it will be evident that, although specific embodiments of the invention have been described herein for purposes of illustration, various modifications may be made without deviating from the spirit and scope of the invention.

We claim:

1. A microemulsion composition for the delivery of hydrophobic compounds to a cell, comprising a mixture of an oil, a hydrophobic compound, and a polyethylene glycol-linked lipid, said mixture surrounded by a monolayer of a polar lipid.

2. The microemulsion of claim 1 wherein the mixture further includes a phospholipid.

3. The microemulsion of claim 2 wherein the phospholipid is phosphatidylcholine.

4. The microemulsion of claim 1 wherein the oil is from a plant.

5. The microemulsion of claim 4 wherein the oil is selected from the group consisting of corn oil, safflower oil, olive oil, and sunflower oil.

6. The microemulsion of claim 1 wherein the oil is a mixture of triacylglyceride and free fatty acids.

7. The microemulsion of claim 1 wherein the monolayer is a phospholipid or a glycolipid.

8. The microemulsion of claim 1 wherein the monolayer consists of 55%–100% by molarity of a phospholipid.

9. The microemulsion of claim 7 wherein the phospholipid is selected from the group consisting of phosphatidylcholine, phosphatidyl glycerol, phosphatidylethanolamine, phosphatidylserine, phosphatidylinositol, phosphatidic acid, and sphingomyelin.

10. The microemulsion of claim 1 wherein the monolayer consists of 0 to 45% by molarity of a steroid selected from the group consisting of cholesterol, PEG cholesterol, coprostanol, cholestano, cholestrane, cholesterol hemisuccinate, and organic acid derivatives of tocopherol.

11. The microemulsion of claim 1 wherein the polyethylene glycol-linked lipid has a molecular weight of between 500 to about 20,000.

12. The microemulsion of claim 1 wherein the polyethylene glycol-linked contains lipids with amino, hydroxyl or sulfhydryl groups.

13. The microemulsion of claim 1 wherein the microemulsion has a size range of about 30 nm to 1000 nm.

14. The microemulsion of claim 1 wherein the monolayer further includes a targeting moiety.

15. The microemulsion of claim 14 wherein the targeting moiety is a biotinylated lipid.

16. The microemulsion of claim 14 wherein the targeting moiety is a streptavidin or an avidin.

17. The microemulsion of claim 14 wherein the targeting moiety is an antibody or antigen-binding portion thereof.

18. The microemulsion of claim 1 wherein the hydrophobic compound is a therapeutic agent.

* * * * *